(12) United States Patent
Capet et al.

(10) Patent No.: US 6,767,921 B2
(45) Date of Patent: Jul. 27, 2004

(54) POLYMORPHIC FORMS OF FASIDOTRIL, THEIR METHODS OF PREPARATION AND PHARMACEUTICAL COMPOSITIONS COMPRISING THEM

(75) Inventors: Marc Capet, Melesse (FR); Gérard Coquerel, Boos (FR); Denis Danvy, Yvetot (FR); Jeanne-Marie Lecomte, Paris (FR); Marie-Noëlle Petit, Mont Saint-Aignan (FR); Jean-Charles Schwartz, Paris (FR)

(73) Assignee: Bioproject, Paris (FR)

( * ) Notice: Subject to any disclaimer, the term of this patent is extended or adjusted under 35 U.S.C. 154(b) by 0 days.

(21) Appl. No.: 10/396,692

(22) Filed: Mar. 26, 2003

(65) Prior Publication Data

US 2003/0203965 A1 Oct. 30, 2003

(30) Foreign Application Priority Data

Mar. 29, 2002 (FR) .......................................... 02 04036

(51) Int. Cl.$^7$ ................................................ A61K 31/36
(52) U.S. Cl. ...................................... 514/464; 549/441
(58) Field of Search .......................... 549/441; 514/464

(56) References Cited

FOREIGN PATENT DOCUMENTS

EP            0 419 327        3/1991

*Primary Examiner*—Amelia Owens
(74) *Attorney, Agent, or Firm*—Stites & Harbison PLLC; B. Aaron Schulman

(57) ABSTRACT

The subject of the present invention is the various polymorphic forms I, II, III, IV of benzyl (S,S)-2-(2-acetylsulphanylmethyl-3-benzo[1,3]dioxol-5-ylpropionyl-amino)propionate, hereinafter called Fasidotril, their methods of preparation and novel pharmaceutical compositions containing them.

17 Claims, 1 Drawing Sheet

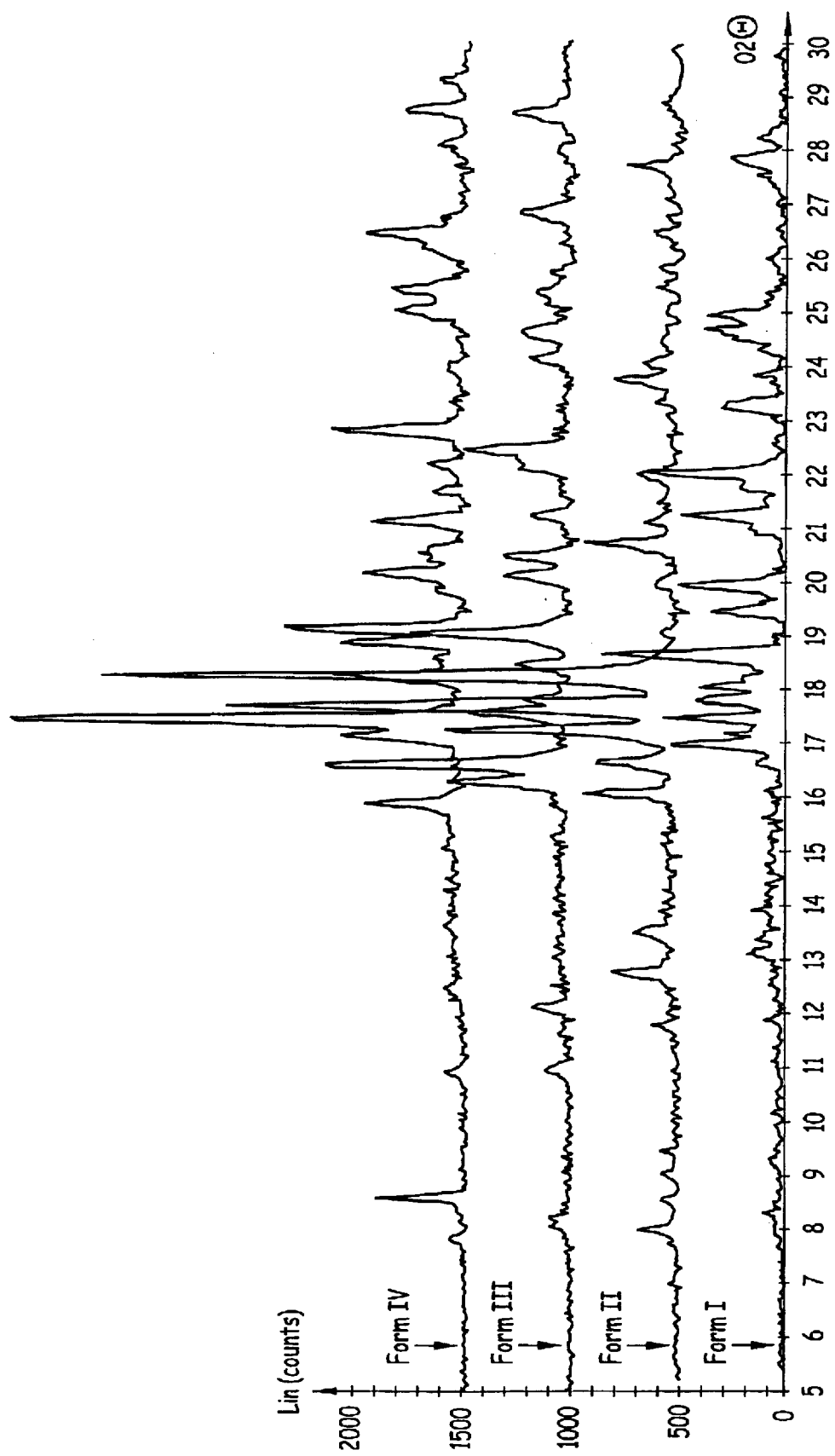

POLYMORPHIC FORMS OF FASIDOTRIL, THEIR METHODS OF PREPARATION AND PHARMACEUTICAL COMPOSITIONS COMPRISING THEM

The subject of the present invention is the various polymorphic forms of benzyl (S,S)-2-(2-acetylsulphanylmethyl-3-benzo[1,3]dioxol-5-ylpropionylamino)propionate, called hereinafter Fasidotril, and the methods for preparing them.

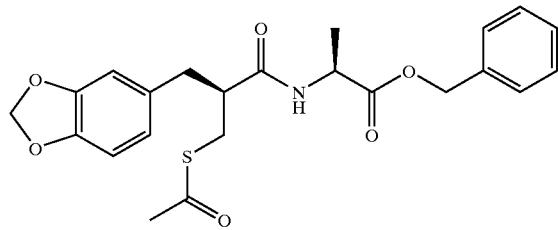

Fasidotril, benzyl (S,S)-2-(2-acetylsulphanylmethyl-3-benzo[1,3]dioxol-5-ylpropionylamino)propionate, may be prepared by applying the methods described in Patent EP 0,419,327 B1 or Patent FR 0014419 filed by Société Civile Bioprojet and has advantageous properties as a mixed inhibitor of the enzymes enkephalinase (EC 3.4.24.11) and angiotensin converting enzyme (EC 3.4.15.1; ACE). It is indeed known that enkephalinase is a peptidase which degrades in particular enkephalins. Methionine and leucine enkephalin are peptides which were discovered in the brain and which are endogenous ligands for the morphine receptor. Moreover, the atrial natriuretic factor (ANF) is an endogenous peptide which exerts vasorelaxing, diuretic and natriuretic effects which are potentially beneficial in the treatment of cardiovascular and renal conditions. ANF is a substrate for enkephalinase and inhibitors of this peptidase slow its degradation, increase its plasma level and induce antihypertensive, diuretic and natriuretic effects (Lecomte et al., Proc. Natl. Ac. Sci. USA 1989, 86:19:7580–4).

It is also known, for example from French Patent No. 2,623,498 filed in the name of the applicant, that some amino acid derivatives exert an inhibitory activity on the enzyme for converting angiotensin I to angiotensin II (ACE), angiotensin II being an active vasomotor substance considered as the agent responsible for various forms of hypertension. These compounds are therefore useful for the treatment of hypertension and of cardiac insufficiency.

It has been discovered that Fasidotril can exist in various polymorphic crystalline forms which differ from each other in their physical and spectroscopic properties, their zones of thermodynamic stability and their methods of preparation. Four of these novel forms are described below and will be designated as form I, form II, form III and form IV, respectively.

It is shown that among these four forms, forms I and II are stable at low and high temperature, respectively, while forms III and IV are unstable and can be easily converted to the stable form I or II depending on the operating conditions chosen.

It is also shown that it is possible to convert form I to form II and to convert form II to form I depending on the operating conditions chosen.

The various polymorphic forms of Fasidotril may be prepared by crystallization, at a temperature of between the freezing point of the solution and the boiling point of the mixture, from a solution of Fasidotril in a solvent chosen from saturated hydrocarbons (for example pentane, cyclohexane) or unsaturated hydrocarbons (for example toluene, xylene), alcohols (for example methanol, ethanol, 2-propanol), ethers (for example diisopropyl ether, diethyl ether), esters (for example ethyl acetate, isopropyl acetate), amides (for example dimethylformamide, N-methylpyrrolidone, dimethylacetamide), nitriles (for example acetonitrile), halogenated solvents (for example dichloromethane, dichloroethane, chlorobenzene), water or a mixture of these solvents. This crystallization may be spontaneous or triggered by slow or rapid cooling, addition of a solvent, of seed crystals consisting of crystallized Fasidotril or another solid product, evaporation or distillation of the solvent. Furthermore, the initial Fasidotril solution may contain other products, for example an isomer of Fasidotril.

In the case, for example, of the preparation by spontaneous crystallization, it is possible to obtain form I by choosing a temperature of less than 25° C., or form II by choosing a higher temperature, for example 50° C., and maintaining this temperature for a sufficient period.

The various stable polymorphic forms of Fasidotril may also be prepared by conversion from one stable or metastable form to another. This conversion may be carried out in solution or in suspension by optionally seeding with a solid form of Fasidotril. This operation is carried out at a temperature between the freezing point of the solvent and its boiling point, in a solvent chosen from saturated hydrocarbons (for example pentane, cyclohexane) or unsaturated hydrocarbons (for example toluene, xylene), alcohols (for example methanol, ethanol, isopropanol), ethers (for example diisopropyl ether, diethyl ether), esters (for example ethyl acetate, isopropyl acetate), amides (for example dimethylformamide, N-methylpyrrolidone, dimethylacetamide), nitriles (for example acetonitrile), water or a mixture of these solvents.

The various polymorphic forms of Fasidotril may be characterized by X-ray diffraction (see FIG. 4), by differential scanning calorimetry, by infrared, by NMR of the solid or by any other method known to persons skilled in the art.

Form I has a novel X-ray powder diffraction spectrum (measurement carried out on a Siemens D5005 diffractometer with a copper anticathode; the results are exploited with the Eva v 7.0 software) with the following characteristic lines (2 theta in °):

17.1; 17.6; 17.9; 18.1; 18.8; 19.5; 20.0; 21.3; 22.1; 23.3; 24.8; 25.0; 27.8

The differential scanning calorimetry spectrum at 2° C./min shows two maxima, one at 110.3° C., the other at 114.1° C. with enthalpies of 40.13 J/g and 65.47 J/g, respectively, and an onset of melting at 108.8° C.

The infrared spectrum as a KBr tablet has the characteristic absorptions at the following wavelengths (in $cm^{-1}$, f for weak, m for average, F for strong):

3280 (F), 3080 (f), 3040 (f), 3000 (f), 2920 (m), 2800 (f), 1730 (F), 1690 (F), 1680 (F), 1640 (F), 1610 (f), 1540 (F), 1500 (F), 1480 (F), 1440 (F), 1400 (f), 1380 (m), 1360 (f), 1330 (m), 1310 (m), 1280 (m), 1260 (F), 1250 (F), 1220 (F), 1200 (F), 1130 (F), 1110 (F), 1060 (F), 1040 (F), 1010 (f), 1000 (f), 960 (F), 940 (f), 930 (m), 900 (m), 860 (f), 810 (m), 790 (m), 750 (F), 720 (f), 700 (F), 680 (f), 620 (F), 600 (f), 580 (f), 540 (f), 520 (f), 480 (f), 460 (f), 450 (f), 430 (f)

Form II has a novel X-ray powder diffraction spectrum (measurement carried out on a Siemens D5005 diffractometer with a copper anticathode; the results are exploited with the Eva v 7.0 software) with the following characteristic lines (2 theta in °):

8.1; 12.9; 16.2; 16.8; 17.3; 17.8; 18.4; 20.8; 23.8; 27.7

The differential scanning calorimetry spectrum at 2° C./min shows a maximum at 114.8° C. with an enthalpy of 101.64 J/g and an onset of melting at 112.6° C.

The infrared spectrum as a KBr tablet has the characteristic absorptions at the following wavelengths (in cm$^{-1}$, f for weak, m for average, F for strong):

3320 (F), 3280 (F), 3080 (f), 3000 (f), 2920 (m), 2880 (m), 2800 (f), 1730 (F), 1690 (F), 1680 (F), 1640 (F), 1540 (F), 1500 (F), 1480 (F), 1440 (F), 1400 (f), 1380 (m), 1360 (m), 1330 (m), 1310 (m), 1280 (m), 1260 (F), 1220 (F), 1200 (F), 1160 (f), 1130 (F), 1110 (F), 1060 (f), 1040 (F), 1010 (f), 1000 (f), 960 (F), 940 (m), 930 (m), 900 (m), 860 (f), 810 (m), 790 (m), 750 (F), 700 (F), 620 (F), 600 (f), 580 (f), 540 (f), 520 (f), 480 (f), 460 (f), 430 (f).

Form III has a novel X-ray powder diffraction spectrum (measurement carried out on a Siemens D5005 diffractometer with a copper anticathode; the results are exploited with the Eva v 7.0 software) with the following characteristic lines (2 theta in °):

11.1; 12.2; 16.4; 16.7; 17.7; 17.9; 18.6; 19.1; 20.2; 20.6; 21.3; 22.2; 22.6; 24.2; 24.7; 26.8; 28.6

The differential scanning calorimetry spectrum at 0.2° C./min shows four maxima at 101.3° C., 103.6° C., 105.9° C. and 113.9° C. with enthalpies of 3.62 J/g, 3.92 J/g, 1.61 J/g and 94.08 J/g, respectively, and onsets at 100.7° C., 103.0° C., 104.8° C. and 112.1° C., respectively.

Form IV has a novel X-ray powder diffraction spectrum (measurement carried out on a Siemens D5005 diffractometer with a copper anticathode; the results are exploited with the Eva v 7.0 software) with the following characteristic lines (2 theta in °):

8.8; 16.0; 17.2; 17.7; 18.4; 19.1; 19.3; 20.3; 21.3; 22.9; 25.1; 25.5; 26.5; 28.8

The differential scanning calorimetry spectrum at 0.2° C./min shows three maxima at 90.4° C., 103.0° C. and 113.5° C. with enthalpies of 1.32 J/g, 12.91 J/g and 96.10 J/g, respectively, with onsets at 87.0° C., 101.5° C. and 111.2° C., respectively.

The present invention also relates to the pharmaceutical compositions containing, as active ingredient, Fasidotril in one of its polymorphic forms.

These compositions can be administered to humans by the oral, parenteral or rectal route.

These pharmaceutical compositions may be in solid or liquid form and may be provided in pharmaceutical dosage forms which are commonly used in human medicine such as, for example, in the form of plain or sugar-coated tablets, gelatin capsules, suppositories or preparations for injection.

The pharmaceutical compositions in accordance with the invention can be administered in unit doses, preferably of 1 to 200 mg of active ingredient and at a daily dosage which may range from 2 to 400 mg of active ingredient.

Advantageously, a pharmaceutical composition may comprise the stable form I or II, but it is also possible to prepare pharmaceutical compositions with forms III or IV.

The subject of the invention is also a method for treating a patient requiring treatment, by inhibiting enkephalinase and the angiotensin converting enzyme.

It relates in particular to a method of treating hypertension and/or cardiac insufficiency in which a pharmaceutical composition comprising one of the forms I, II, III or IV of Fasidotril is administered to a patient.

Preferably, and unless a delayed release form is used, this method envisages the administration of a daily dosage of between 2 and 400 mg of Fasidotril, preferably administered in the form of unit doses of 1 to 200 mg.

The subject of the invention is also the use of one of the forms I to IV to prepare a pharmaceutical composition as described above for the treatment of hypertension and/or cardiac insufficiency.

The examples given below illustrate the present invention without limiting it as a result.

In the following examples, Fasidotril is synthesized by any of the methods suited to Fasidotril and described in Patents EP 419 327 or FR 0014419. The purities of the polymorphic forms obtained after using the following examples are higher than 95% (precision limit of the analytical technique used).

FIG. 1 represents the powder diffraction spectra of forms I, II, III and IV.

EXAMPLE 1

Fasidotril Form III

A round-bottomed flask containing 1 g of Fasidotril is heated until the product melts. The round-bottomed flask is rapidly cooled by immersing in an ice-water bath. 1 g of Fasidotril is thus obtained whose powder diffraction spectrum is in conformity with that of form III.

EXAMPLE 2

Fasidotril Form IV 1 g of Fasidotril is dissolved in 15 ml of 2-propanol by heating to a temperature in the region of 70° C. 20 ml of heptane cooled to −70° C. are added to this solution. The temperature drops to 25° C. and crystallization occurs rapidly. The medium is stirred for a further 4 minutes, filtered and dried under reduced pressure (20 mmHg) at 25° C. 0.77 g of Fasidotril is thus obtained whose powder diffraction spectrum is in conformity with that of form IV.

EXAMPLE 3

Fasidotril Form IV

A round-bottomed flask containing a solution of 2 g of Fasidotril in 35 ml of 2-propanol heated to a temperature of 80° C., is suddenly immersed in a bath of acetone saturated with dry ice. Precipitation is instant. After stirring for 2 minutes, the suspension is filtered and dried under reduced pressure (20 mmHg) at 25° C. 1.75 g of Fasidotril are thus obtained whose powder diffraction spectrum is in conformity with that of form IV.

EXAMPLE 4

Fasidotril Form II

A stoppered glass bottle containing 0.2 g of Fasidotril form IV is left for 3 days in a ventilated oven at 94° C. 0.2 g of Fasidotril is thus obtained whose powder diffraction spectrum is in conformity with that of form II.

EXAMPLE 5

Fasidotril Form III

A sublimator having an inner diameter of 45 mm, containing 2 g of Fasidotril is heated under vacuum at a pressure of 0.1 mmHg. After stopping the heating and returning to atmospheric pressure, the solid deposited on the condenser is recovered. 0.4 g of Fasidotril is thus obtained whose powder diffraction spectrum is in conformity with that of form III.

EXAMPLE 6

Fasidotril Form I 5 g of Fasidotril are dissolved in 20 ml of acetone by heating to a temperature in the region of 50° C. The heating is stopped and the solution thus obtained is allowed to cool.

Crystallization occurs at 32° C. The stirring is maintained and the suspension is cooled to −5° C. The solid is separated by filtration and dried under reduced pressure (20 mmHg) at 20° C. 4.66 g of Fasidotril are thus obtained whose powder diffraction spectrum is in conformity with that of form I.

EXAMPLE 7
Fasidotril Form I 30 g of Fasidotril are dissolved in 120 ml of ethyl acetate by heating to a temperature in the region of 52° C. The heating is stopped and the solution thus obtained is cooled with the aid of a water bath at 10° C. Rapid crystallization occurs at 31° C. The suspension is kept stirred at 30° C. for 5 minutes, and is then cooled to 0° C. The solid is separated by filtration, rinsed with 20 ml of ethyl acetate at 5° C. and dried under reduced pressure (20 mmHg) at 20° C. 25.40 g of Fasidotril are thus obtained whose powder diffraction spectrum is in conformity with that of form I.

EXAMPLE 8
Fasidotril Form I 2 mg of Fasidotril form II are added to a suspension of 1 g of Fasidotril form IV in 20 ml of a dichloromethane/2-propanol (2/18 by volume) mixture. The mixture is stirred for eleven days at 20° C. The insoluble matter is separated by filtration and dried under vacuum to give 0.6 g of Fasidotril whose powder diffraction spectrum is in conformity with that of form I.

EXAMPLE 9
Fasidotril Form I 2 mg of Fasidotril form IV are added to a suspension of 1 g of Fasidotril form III in 20 ml of a dichloromethane/2-propanol (2/18 by volume) mixture. The mixture is stirred for twelve days at 20° C. The insoluble matter is separated by filtration and dried under vacuum to give 0.5 g of Fasidotril whose powder diffraction spectrum is in conformity with that of form I.

EXAMPLE 10
Fasidotril Form I 13.88 g of Fasidotril are dissolved in 207 ml of 2-propanol by heating to a temperature in the region of 70° C. The solution thus obtained is cooled to a temperature in the region of 50° C. and crystallization is initiated by introducing a few crystals of Fasidotril form I. The suspension is cooled over two hours to a temperature in the region of 35° C., and is then kept at this temperature for one hour thirty minutes. The solid is separated by filtration, rinsed with 15 ml of 2-propanol and dried under reduced pressure (20 mmHg) at 25° C. 11.16 g of Fasidotril are thus obtained whose powder diffraction spectrum is in conformity with that of form I.

EXAMPLE 11
Fasidotril Form I 2 mg of Fasidotril form I are added to a suspension of 1 g of Fasidotril form IV in 20 ml of a dichloromethane/2-propanol (2/18 by volume) mixture. The mixture is stirred for twelve days at 20° C. The insoluble matter is separated by filtration and dried under vacuum to give 0.34 g of Fasidotril whose powder diffraction spectrum is in conformity with that of form I.

EXAMPLE 12
Fasidotril Form II 2 mg of Fasidotril form II are added to a suspension of 1 g of Fasidotril form I in 20 ml of 2-propanol. The mixture is stirred for five days at 45° C. The insoluble matter is separated by filtration, and dried under vacuum to give 0.58 g of Fasidotril whose powder diffraction spectrum is in conformity with that of form II.

EXAMPLE 13
Fasidotril Form II 2 mg of Fasidotril form III are added to a suspension of 0.5 g of Fasidotril form I in 10 ml of 2-propanol. The mixture is stirred for four days at 45° C. The insoluble matter is separated by filtration, and dried under vacuum to give 0.17 g of Fasidotril whose powder diffraction spectrum is in conformity with that of form II.

EXAMPLE 14
Fasidotril Form I 2 mg of Fasidotril form I are added to a suspension of 1 g of Fasidotril form II in 20 ml of a dichloromethane/2-propanol (1/16 by volume) mixture. The mixture is stirred for fourteen days at 20° C. The insoluble matter is separated by filtration and dried under vacuum to give 0.6 g of Fasidotril whose powder diffraction spectrum is in conformity with that of form I.

EXAMPLE 15
Fasidotril Form I 2 mg of Fasidotril form I are added to a suspension of 1 g of Fasidotril form III in 20 ml of a dichloromethane/2-propanol (2/18 by volume) mixture. The mixture is stirred for twelve days at 20° C. The insoluble matter is separated by filtration and dried under vacuum to give 0.51 g of Fasidotril whose powder diffraction spectrum is in conformity with that of form I.

What is claimed is:

1. Polymorphic forms of benzyl (S,S)-2-(2-acetylsulphanylmethyl-3-benzo[1,3]dioxol-5-ylpropionylamino)-propionate

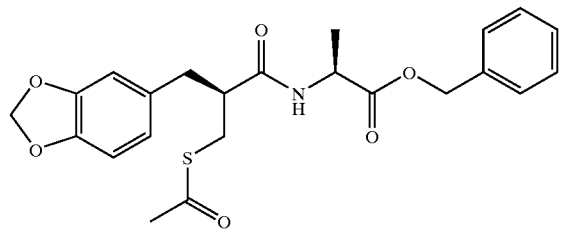

characterized by the X-ray powder diffraction spectrum (2 theta in °)

form I: 17.1; 17.6; 17.9; 18.1; 18.8; 19.5; 20.0; 21.3; 22.1; 23.3; 24.8; 25.0; 27.8 form II: 8.1; 12.9; 16.2; 16.8; 17.3; 17.8; 18.4; 20.8; 23.8; 27.7 form III: 11.1; 12.2; 16.4; 16.7; 17.7; 17.9; 18.6; 19.1; 20.2; 20.6; 21.3; 22.2; 22.6; 24.2; 24.7; 26.8; 28.6 form IV: 8.8; 16.0; 17.2; 17.7; 18.4; 19.1; 19.3; 20.3; 21.3; 22.9; 25.1; 25.5; 26.5; 28.8 and their differential scanning calorimetry spectra form I (2° C./min): two maxima, one at 110.3° C., the other at 114.1° C. with enthalpies of 40.13 J/g and 65.47 J/g, respectively, and an onset of melting at 108.8° C.

form II (2° C./min): maximum at 114.8° C. with an enthalpy of 101.64 J/g and an onset of melting at 112.6° C.

form III (0.2° C./min): four maxima at 101.3° C., 103.6° C., 105.9° C. and 113.9° C. with enthalpies of 3.62 J/g, 3.92 J/g, 1.61 J/g and 94.08 J/g, respectively, and onsets at 100.7° C., 103.0° C., 104.8° C. and 112.1° C., respectively form IV (0.2° C./min): three maxima at 90.4° C., 103.0° C. and 113.5° C. with enthalpies of 1.32 J/g, 12.91 J/g and 96.10 J/g, respectively, with onsets at 87.0° C., 101.5° C. and 111.2° C., respectively.

2. Stable polymorphic form I of benzyl (S,S)-2-(2-acetylsulphanylmethyl-3-benzo[1,3]dioxol-5-ylpropionylamino)propionate, characterized by the X-ray powder diffraction spectrum (2 theta in °)

17.1; 17.6; 17.9; 18.1; 18.8; 19.5; 20.0; 21.3; 22.1; 23.3; 24.8; 25.0; 27.8 the differential scanning calorimetry spectrum (2° C./min): two maxima, one at 110.3° C., the other at 114.1° C. with enthalpies of 40.13 J/g and 65.47 J/g, respectively, and an onset of melting at 108.8° C.

and the infrared spectrum as a KBr tablet (absorption in cm$^{-1}$) 3280 (F), 3080 (f), 3040 (f), 3000 (f), 2920 (m), 2800 (f), 1730 (F), 1690 (F), 1680 (F), 1640 (F), 1610 (f), 1540 (F), 1500 (F), 1480 (F), 1440 (F), 1400 (f), 1380 (m), 1360 (f), 1330 (m), 1310 (m), 1280 (m), 1260 (F), 1250 (F), 1220 (F), 1200 (F), 1130 (F), 1110 (F), 1060 (f), 1040 (F), 1010 (f), 1000 (f), 960 (F), 940 (f), 930 (m), 900 (m), 860 (f), 810 (m), 790 (m), 750 (F), 720 (f), 700 (F), 680 (f), 620 (F), 600 (f), 580 (f), 540 (f), 520 (f), 480 (f), 460 (f), 450 (f), 430 (f).

3. Stable polymorphic form II of benzyl (S,S)-2-(2-acetylsulphanylmethyl-3-benzo[1,3]dioxol-5-ylpropionylamino)propionate, characterized by the X-ray powder diffraction spectrum (2 theta in °)

8.1; 12.9; 16.2; 16.8; 17.3; 17.8; 18.4; 20.8; 23.8; 27.7 the differential scanning calorimetry spectrum form II (2° C./min): maximum at 114.8° C. with an enthalpy of 101.64 J/g and an onset of melting at 112.6° C.

and the infrared spectrum as a KBr tablet (absorption in cm$^{-1}$)

3320 (F), 3280 (F), 3080 (f), 3000 (f), 2920 (m), 2880 (m), 2800 (f), 1730 (F), 1690 (F), 1680 (F), 1640 (F), 1540 (F), 1500 (F), 1480 (F), 1440 (F), 1400 (f), 1380 (m), 1360 (m), 1330 (m), 1310 (m), 1280 (m), 1260 (F), 1220 (F), 1200 (F), 1160 (f), 1130 (F), 1110 (F), 1060 (f), 1040 (F), 1010 (f), 1000 (f), 960 (F), 940 (m), 930 (m), 900 (m), 860 (f), 810 (m), 790 (m), 750 (F), 700 (F), 620 (F), 600 (f), 580 (f), 540 (f), 520 (F), 480 (f), 460 (f), 430 (f).

4. Method for preparing the polymorphic forms of benzyl (S,S)-2-(2-acetylsulphanylmethyl-3-benzo[1,3]dioxol-5-ylpropionylamino)propionate of claim 1, and in particular of the stable forms I or II by crystallization, at a temperature between the freezing point of the solution and the boiling point of the mixture, from a solution of benzyl (S,S)-2-(2-acetylsulphanylmethyl-3-benzo[1,3]dioxol-5-ylpropionylamino)propionate in a solvent chosen from saturated or unsaturated hydrocarbons, alcohols, ethers, esters, amides, nitriles, halogenated solvents, water or a mixture of these solvents, the initial solution of benzyl (S,S)-2-(2-acetylsulphanylmethyl-3-benzo[1,3]dioxol-5-ylpropionylamino)propionate optionally containing other products.

5. Method of preparation according to claim 4, characterized in that said crystallization is a crystallization which is spontaneous or which is triggered by slow or rapid cooling, addition of a solvent, of seed crystals consisting of crystallized benzyl (S,S)-2-(2-acetylsulphanylmethyl-3-benzo[1,3]dioxol-5-ylpropionylamino)propionate or of another solid product, evaporation or distillation of the solvent, it being possible for the initial solution of benzyl (S,S)-2-(2-acetylsulphanylmethyl-3-benzo[1,3]dioxol-5-ylpropionylamino)propionate to contain other products.

6. Method of preparation according to either of claim 4, characterized in that the solvent is chosen from one of the groups consisting of pentane, cyclohexane, toluene, xylene, methanol, ethanol, 2-propanol, diisopropyl ether, diethyl ether, ethyl acetate, isopropyl acetate, dimethylformamide, N-methylpyrrolidone, dimethylacetamide, acetonitrile, dichloromethane, dichloroethane, chlorobenzene, water or a mixture of these solvents.

7. Method for preparing the stable forms I or II of benzyl (S,S)-2-(2-acetylsulphanylmethyl-3-benzo[1,3]dioxol-5-ylpropionylamino)propionate of claims 1, by crystallization of one form into another, in solution or in suspension, optionally by seeding with a solid form of benzyl (S,S)-2-(2-acetylsulphanylmethyl-3-benzo[1,3]dioxol-5-ylpropionylamino)propionate, at a temperature between the freezing point of the solvent and its boiling point, in a solvent chosen from saturated or unsaturated hydrocarbons, alcohols, ethers, esters, amides, nitriles, water or a mixture of these solvents.

8. Method of preparation according to claim 7, characterized in that the medium is chosen from the group consisting of pentane, cyclohexane, toluene, xylene, methanol, ethanol, isopropanol, diisopropyl ether, diethyl ether, ethyl acetate, isopropyl acetate, dimethylformamide, N-methylpyrrolidone, dimethylacetamide, acetonitrile, water or a mixture of these solvents.

9. Pharmaceutical compositions containing, as active ingredient, benzyl (S,S)-2-(2-acetylsulphanylmethyl-3-benzo[3]dioxol-5-ylpropionylamino)propionate in one of its polymorphic forms as defined in claim 1.

10. Pharmaceutical compositions containing, as active ingredient, benzyl (S,S)-2-(2-acetylsulphanylmethyl-3-benzo[1,3]dioxol-5-ylpropionylamino)propionate in the form of its stable polymorphic forms as defined in claims 2.

11. A method of using benzyl (S,S)-2-(2-acetylsulphanylmethyl-3-benzo[1,3]dioxol-5-ylpropionylamino)propionate in the form of one of its polymorphic forms as defined in claim 1, comprising preparing said polymorphic form as a pharmaceutical composition an using said composition for the treatment of hypertension and/or cardiac insufficiency.

12. A method of using benzyl (S,S)-2-(2-acetylsulphanylmethyl-3-benzo[1,3]dioxol-5-ylpropionylamino)propionate in the form of one of its polymorphic forms as defined in claim 2, comprising preparing said polymorphic form as a pharmaceutical composition and using said composition for the treatment of hypertension and/or cardiac insufficiency.

13. Method of preparation according to claim 5, characterized in that the solvent is chosen from one of the groups consisting of pentane, cyclohexane, toluene, xylene, methanol, ethanol, 2-propanol, diisopropyl ether, diethyl ether, ethyl acetate, isopropyl acetate, dimethylformamide, N-methylpyrrolidone, dimethylacetamide, acetonitrile, dichloromethane, dichloroethane, chlorobenzene, water or a mixture of these solvents.

14. Pharmaceutical compositions containing, as active ingredient, benzyl (S,S)-2-(2-acetylsulphanylmethyl3-benzo[1,3]dioxol-5-ylpropionylamino)propionate in the form of one of its stable polymorphic forms as defined in claim 3.

15. A method of using benzyl (S,S)-2-(-acetylsulphanyl-methyl-3-benzo[1,3]dioxol-5-ylpropionylamino)propionate in the form of one of its polymorphic forms as defined in claim 3, comprising preparing said polymorphic form as a pharmaceutical composition and using said composition for the treatment of hypertension and/or cardiac insufficiency.

16. The method of claim 4 wherein the optionally contained other product is an isomer of benzyl (S,S)-2-(2-acetylsuphanylmethyl-3-benzo[1,3]dioxol-5-ylpropionylamino)propionate.

17. The method of claim 5 wherein the other product contained is an isomer of benzyl (S,S)-2-(2-acetylsulphanylmethyl-3-benzo[1,3]dioxol-5-ylpropionylamino)propionate

* * * * *